United States Patent [19]

Henrick

[11] Patent Number: 5,389,651

[45] Date of Patent: Feb. 14, 1995

[54] NITROGEN-CONTAINING HETEROCYCLYL-OXY AND -THIO COMPOUNDS USEFUL AS PESTICIDES

[75] Inventor: Clive A. Henrick, Palo Alto, Calif.

[73] Assignee: Sandoz Ltd., Basle, Switzerland

[21] Appl. No.: 77,835

[22] Filed: Jul. 27, 1987

Related U.S. Application Data

[63] Continuation-in-part of Ser. No. 856,563, Apr. 28, 1986, abandoned, which is a continuation-in-part of Ser. No. 756,873, Jul. 18, 1985, abandoned.

[51] Int. Cl.⁶ ............... C07D 213/643; C07D 213/69; A01N 43/40
[52] U.S. Cl. ..................... 514/345; 514/348; 546/296; 546/302; 544/318; 548/182; 548/183
[58] Field of Search ............... 546/302, 296; 514/345, 514/348

[56] References Cited

U.S. PATENT DOCUMENTS

| | | | |
|---|---|---|---|
| 3,255,193 | 6/1966 | Brokke et al. | 544/318 |
| 3,535,328 | 10/1970 | Zielinski | 546/275 |
| 3,894,862 | 7/1975 | Whitaker et al. | 71/94 |
| 4,326,879 | 4/1982 | Spencer et al. | 504/254 |
| 4,460,588 | 7/1984 | Serban et al. | 514/274 |
| 4,714,706 | 12/1987 | Kisida et al. | 514/345 |

FOREIGN PATENT DOCUMENTS

| | | | |
|---|---|---|---|
| 128648 | 12/1984 | European Pat. Off. | 544/318 |
| 861836 | 11/1986 | Greece | 514/274 |
| 84-01945 | 5/1984 | WIPO | 546/300 |

*Primary Examiner*—Alan L. Rotman
*Attorney, Agent, or Firm*—Robert S. Honor; Melvyn M. Kassenoff

[57] ABSTRACT

Compounds of the formula

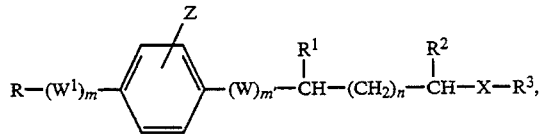

wherein
R is hydrogen; $C_{1-8}$alkyl; $C_{2-8}$alkenyl; $C_{3-8}$alkadienyl; $C_{2-8}$alkynyl; $C_{4-8}$alkadiynyl; $C_{2-10}$(alkoxyalkyl); $C_{2-10}$(alkylthioalkyl); $C_{3-8}$cycloalkyl and $C_{4-12}$(cycloalkylalkyl); optionally substituted by 1 to 6 halos,
$R^1$ is hydrogen or $C_{1-8}$alkyl,
$R^2$ is hydrogen, $C_{1-8}$alkyl or halo,
$R^3$ is

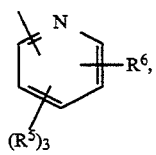

wherein each
$R^5$ and $R^6$, are independently hydrogen, halo, $C_{1-8}$alkyl, optionally substituted by 1 to 6 halos, $C_{1-8}$alkoxy, $C_{1-8}$alkylthio or nitro,
W is $-O-$, $-S-$, $-NR^4-$ or $-CO-$,
$W^1$ is $-O-$, $-S-$, $-SO-$, $-SO_2-$, $-NR^4-$ or $-CO-$,
X is $-O-$, $-S-$, $-NR^4-$ or

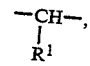

wherein
$R^1$ is hydrogen or $C_{1-8}$alkyl,
Z is hydrogen, $C_{1-8}$alkyl optionally substituted by 1 to 6 halos,
m is 0 or 1,
m' is 0 or 1, and
n is 0, 1 or 2,
wherein each $R_4$ is independently hydrogen or $C_{1-8}$ alkyl, said compounds are useful as pesticides, i.e., insecticides and acaricides.

26 claims, No Drawings

NITROGEN-CONTAINING HETEROCYCLYL-OXY AND -THIO COMPOUNDS USEFUL AS PESTICIDES

This is a continuation-in-part of application Ser. No. 06/856,563, filed Apr. 28, 1986 and now abandoned, which is a continuation-in-part of application Ser. No. 06/756,873, filed Jul. 18, 1985 and, now abandoned.

This invention relates to novel nitrogen-containing heterocyclic compounds of the formula:

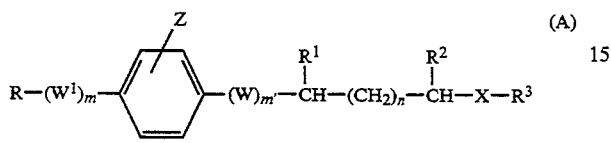

wherein
each of m and m' is zero or one;
n is zero, one or two;
W is oxygen, sulfur, $NR^4$ or carbonyl;
$W^1$ is oxygen, sulfur, $NR^4$, carbonyl, sulfinyl or sulfonyl;
X is oxygen, sulfur, $NR^4$ or $CH(R^1)$;
Z is hydrogen, lower alkyl, lower haloalkyl or halogen;
R is hydrogen, lower alkyl, lower alkenyl, lower alkynyl, lower haloalkyl, lower haloalkenyl, lower haloalkynyl, lower alkoxyalkyl, lower alkylthioalkyl, cycloalkyl, halocycloalkyl, cycloalkylalkyl, heterocycloalkyl or heterocycloalkylalkyl;
each of $R^1$ and $R^4$ is independently hydrogen or lower alkyl;
$R^2$ is hydrogen, lower alkyl or halogen; and
$R^3$ is

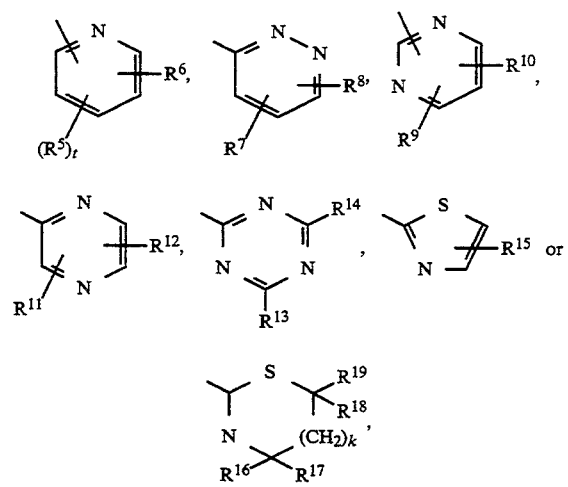

in which
k is zero or one;
t is zero, one, two or three;
each of $R^5$, $R^6$, $R^7$, $R^8$, $R^9$, $R^{10}$, $R^{11}$, $R^{12}$, $R^{13}$, $R^{14}$ and $R^{15}$ is independently hydrogen, halogen, lower alkyl, lower haloalkyl, lower alkoxy, lower alkylthio or nitro; and
each of $R^{16}$, $R^{17}$, $R^{18}$ and $R^{19}$ is independently hydrogen or methyl.

The present invention also encompasses the use of the compounds of formula A for the control of pests, and in particular for the control of insects.

In the description hereinafter and the appended claims, each of m, m', n, R-$R^{19}$, W, $W^1$, X and Z is as defined above, unless otherwise specified.

Preferred compounds of formula A are those formula A', i.e., of formula A
wherein
R is $C_{4-8}$alkyl, $C_{4-8}$alkenyl, $C_{4-8}$alkadienyl, $C_{4-8}$alkynyl or $C_{4-8}$alkadiynyl,
$R^1$ is hydrogen or $C_{1-5}$alkyl,
$R^2$ is hydrogen, $C_{1-5}$alkyl or halo, with the proviso that at least one of $R^1$ and $R^2$ is hydrogen,
$R^3$ is

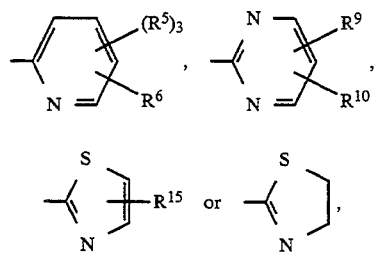

wherein each
$R^5$, $R^6$, $R^9$, $R^{10}$ and $R^{15}$ is independently hydrogen, halo, $C_{1-8}$alkyl, $C_{1-8}$alkoxy, $C_{1-8}$alkylthio, nitro, methyl substituted by 1 to 3 halos, ethyl substituted by 1 to 5 halos or $C_{3-8}$alkyl substituted by 1 to 6 halos,
W is oxygen or sulfur,
$W^1$ is oxygen or sulfur,
X is oxygen or sulfur, and
Z is hydrogen, $C_{1-5}$alkyl, halo, methyl substituted by 1 to 3 halos, ethyl substituted by 1 to 5 halos or $C_{3-5}$alkyl substituted by 1 to 6 halos.

Preferred compounds of formula A' are those wherein (i) $R^1$ is hydrogen or methyl, $R^2$ is hydrogen or methyl, with the proviso that at least one of $R^1$ and $R^2$ is hydrogen, each $R^5$, $R^6$, $R^9$, $R^{10}$ and $R^{15}$ is independently hydrogen or halo, W is oxygen, and n is 0, (ii) of (i) wherein R is $C_{4-8}$alkyl, $C_{4-8}$alkenyl or $C_{4-8}$alkadienyl, and each $R^5$, $R^9$, $R^{10}$ and $R^{15}$ is hydrogen, (iii) of (ii) wherein R is 1-methylpropyl, 1-methylbutyl (i.e., 1-methyl-n-butyl), 1,3-dimethylbutyl (i.e., 1,3-dimethyl-n-butyl) or 3-methyl-2-butenyl, and $R^1$ is hydrogen, (iv) of (iii) wherein R is 1-methylpropyl, 1-methylbutyl or 1,3-dimethylbutyl, (v) of (iv) wherein $R^3$ is

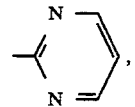

(vi) of (iv) wherein $R^3$ is (vii) of (iv) wherein $R^3$ is

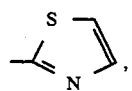

(viii) of (iii) wherein $R^3$ is

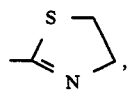

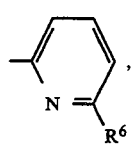

and (ix) of (viii) wherein R is 1-methylpropyl, 1-methylbutyl or 3-methyl-2-butenyl, X is oxygen, and $W^1$ is oxygen.

The compounds of formula A can be prepared by methods known in the art, such as those described in European Patent Application 128,648 and UK Patent Application 2 140 010, for example, and as outlined below:

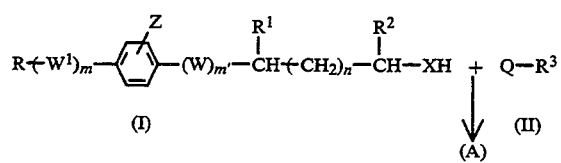

In the above synthesis, an alcohol, thiol or amine of formula I is reacted with a compound of formula II, wherein Q is chlorine, bromine, iodine, mesyloxy or tosyloxy, in an organic solvent such as N-methylpyrrolidone, dimethylformamide or tetrahydrofuran and at a reaction temperature of between 0° and 140°, preferably at between 10° and 110°, in the presence of a base such as potassium carbonate or sodium hydroxide. Alternatively, the salt of formula I is prepared with sodium hydride and this salt is reacted with a halide of formula II.

In a second synthetic method, a compound of formula III is reacted with an alcohol, thiol or amine formula IV, or the sodium salt thereof, following the same general parameters and procedures as described above.

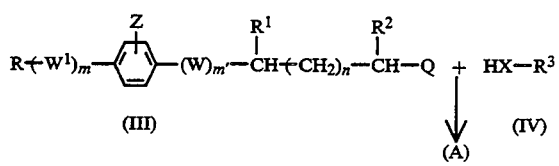

Compounds of formula A wherein $R^2$ is a halogen atom, X is sulfur and each of W and $W^1$ is oxygen can be prepared by reacting the corresponding non-halogenated compounds with a halogenating agent such as N-halosuccinimide, preferrably in an equimolar or greater amount. The reaction may be carried out in an inert solvent, such as carbon tetrachloride, 1,2-dichloroethane or methylene chloride, and if desired, in the presence of a radical initiator.

Compounds of formula A wherein $W^1$ is sulfinyl are prepared by reacting a compound of formula A or an intermediate of formula III wherein $W^1$ is sulfur with one equivalent of sodium periodate or m-chloroperbenzoic acid in a solvent such as methanol or methylene chloride. Compounds where $W^1$ is sulfonyl are prepared in the same manner, except that two equivalents of m-chloroperbenzoic acid are used. Alternatively, either hydrogen peroxide in warm acetic acid or excess hydrogen peroxide with selenium dioxide is used as the oxidant.

The starting alcohols of formula I may be produced by per se conventional procedures, of which typical examples are outlined in European Patent Publication 128,648, for example, and are shown below (W' is oxygen or sulfur, alk is lower alkyl and Q is halogen).

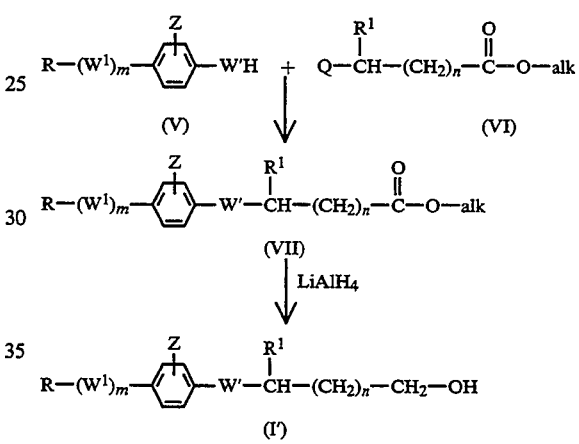

Procedure (2):

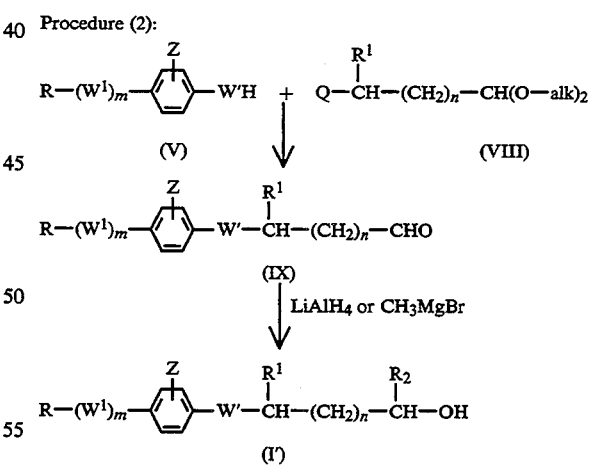

The starting compounds of formula III may be prepared by conventional methods, such as by the halogenation or mesylation of an alcohol of formula I or by the following procedure, for example.

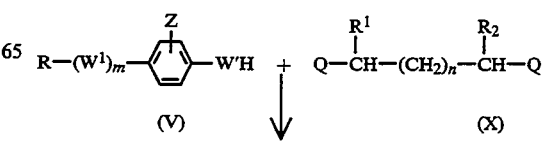

-continued

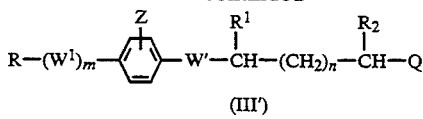
(III')

The compounds of the present invention of formula A can have one or more asymmetric carbon atoms. The present invention includes each of the optical isomers and racemic mixtures thereof. In the examples hereinafter, unless otherwise specified, the compound prepared is a racemic mixture.

The compounds of the present invention of formula A are useful pest control agents, particularly for the control of insects, mites, ticks and helminths. The utility of these compounds as pest control agents is believed to be attributable to their juvenile hormone activity. They are preferably applied to the immature pest, namely during the embryo, larval or prepupal stage, in view of their effect on metamorphosis and otherwise abnormal development leading to death and inability to reproduce.

These compounds can be effective control agents for insects of, for example, the orders Lepidoptera, Hemiptera, Homoptera, Coleoptera, Diptera, Orthoptera, and Siphonaptera, and other insects, as well as mites and ticks of the class Acari, including mites of the families Tetranychidae or Tarsonemidae and ticks of the families Argasidae and Ixodidae.

These compounds are also useful as anthelmintic agents against endoparasites and ectoparasites of warm-blooded animals and against parasites of plants, such as, for example, intestinal and extraintestinal nematodes of the families Ascaridae and Trichostrongylidae and plant parasitic nematodes of the families Heteroderidae and Tylenchidae.

The compounds can be applied to the pest or its locus in a pest controlling amount, usually of the order of 0.1 μg to 100 μg per insect, mite or tick.

In the use of the compounds of formula A for combatting pests, a compound of formula A, or a mixture thereof, can be combined with a carrier substance for application to the locus. The carrier can be liquid or solid and include adjuvants such as wetting agents, dispersing agents and other surface active agents. The compounds can be used in formulations such as wettable powders, solutions, dusts, granules, emulsifiable concentrates and the like. Suitable solid carriers include natural and synthetic silicates and clays, carbon or charcoal granules, natural and synthetic resins, waxes and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to 90.0 percent, by weight. Generally, a concentration of less than 25 percent of the active compound is employed.

The compounds of formula A can be combined with cyclodextrin to make a cyclodextrin inclusion complex for application to the pest or its locus. The compounds of the present invention can be used in combination with other pesticides such as the synthetic pyrethroids, carbamates, phosphates and insect growth regulators, or with insect attractants.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to six halogen atoms.

The term "lower alkenyl" refers to an alkenyl group, straight or branched, having a chain length of two to eight carbon atoms and one or two ethylenic bonds. The term "lower haloalkenyl" refers to a lower alkenyl group substituted with one to six halogen atoms.

The term "lower alkynyl" refers to an alkynyl group, straight or branched, having a chain length of two to eight carbon atoms and one or two acetylenic bonds. The term "lower haloalkynyl" refers to a lower alkynyl group substituted with one to six halogen atoms.

The term "lower alkoxy" refers to an alkoxy group, straight or branched, having a chain length of one to eight carbon atoms.

The term "lower alkoxyalkyl" refers to an alkyl group substituted at one of the-carbon atoms by an alkoxy group, straight or branched, the total number of carbon atoms being not greater than ten.

The term "lower alkylthio" refers to an alkylthio group, straight or branched, having a chain length of one to eight carbon atoms.

The term "lower alkylthioalkyl" refers to a lower alkyl group substituted at one of the carbon atoms by an alkylthio group, straight or branched, the total number of carbon atoms being not greater than ten.

The term "cycloalkyl" refers to a cycloalkyl group of three to eight cyclic carbon atoms. The term "cycloalkylalkyl" refers to a lower alkyl group wherein one hydrogen atom is replaced by a lower alkyl group, the total number of carbon atoms being from four to twelve. The term "halocycloalkyl" refers to a cycloalkyl group substituted with one to six halogen atoms.

The term "heterocycloalkyl" refers to a heterocycloalkyl group, saturated or unsaturated, of two to six carbon atoms and one to three atoms selected from nitrogen, oxygen or sulfur. The term "heterocycloalkylalkyl" refers to a lower alkyl group wherein one hydrogen is replaced by a group, the total number of carbon atoms being from three to twelve.

The following examples are provided to illustrate the practice of the present invention. Temperature is given in degrees Centigrade. "RT" means room temperature.

EXAMPLE 1

To a mixture of sodium hydride (0.08 g) in 5 ml of tetrahydrofuran (THF) and 2 ml of hexamethylphosphoramide (HMPA), cooled in an ice bath, is added, dropwise, 2-methyl-2-[4-(1-methylpropoxy)phenoxy]ethanol (0.63 g). The mixture is stirred at RT for 2 hours, after which a solution of 2-chloropyridine (0.38 g) in 5 ml of THF is added and the mixture is stirred at 60° for 3 hours. The THF is then removed by rotoevaporation and the residue is purified by column chromatography on silica gel to give the product, 2-{2-methyl-2-[4-(1-methylpropoxy)phenoxy]ethoxy}pyridine, MS m/e 302 (M+).

nmr (CDCl$_3$) δ0.8–1.8 (m, 11H), 3.9–4.8 (m, 4H), 6.6–7.0 (m, 6H), 7.3–7.7 (m, 1H) and 8.1–8.3 ppm (m, 1H).

Following the above procedures, the sodium salt of 1-methyl-2-[4-(1-methylpropoxy)phenoxy]ethanol is prepared and reacted with 2-chloropyridine to give 2-{1-methyl-2-[4-(1-methylpropoxy)phenoxy]ethoxy}pyridine, MS m/e 302 (M+).

nmr (CDCl₃) δ0.8–1.8 (m, 11H), 3.9–4.3 (m, 3H), 5.4–5.8 (m, 1H), 6.7–7.0 (m, 6H), 7.3–7.7 (m, 1H) and 8.1–8.3 ppm (2d, 1H).

In the same manner, the sodium salt of 2-[4-(1-methylpropoxy)phenoxy]ethanol and 2-chloropyridine are reacted together to give 2-{2-[4-(1-methylpropoxy)phenoxy]ethoxy}pyridine, MS m/e 288} (M+).

nmr (CDCl₃) δ0.8–1.9 (m, 8H), 4.1–4.4 (m, 3H), 4.6–4.8 (m, 2H), 6.7–7.0 (m, 6H), 7.3–7.7 (m, 1H) and 8.1–8.3 ppm (m, 1H).

EXAMPLE 2

To a mixture of sodium hydride (0.13 g) in 5 ml of THF and 5 ml of HMPA, cooled in an ice bath, is added, dropwise, 2-[4-(3-methyl-2-butenoxy)phenoxy]ethanol (1.00 g) in 5 ml of THF. The mixture is stirred at RT for 1 hour, after which 2-chloropyridine (0.61 g) is added and the mixture is stirred at 60° for 2 hours. The solvent is removed by rotoevaporation. The residue is taken up in ether, washed with water, dried and concentrated, and the remaining oil is purified by column chromatography to give 2-{2-[4-(3-methyl-2-butenoxy)phenoxy]ethoxy}pyridine, MS m/e 300 (M+).

nmr (CDCl₃) δ1.8 (2s, 6H), 4.1–4.7 (m, 6H), 5.4 (t, 1H), 6.8–6.9 (m, 6H), 7.3–7.7 (m, 1H) and 8.0–8.2 ppm (m, 1H).

Following the above procedures, the sodium salt of 1-methyl-2-[4-(3-methyl-2-butenoxy)phenoxy]ethanol is prepared and reacted with 2-chloropyridine to give 2-{1-methyl-2-[4-(3-methyl-2-butenoxy)phenoxy]ethoxy}pyridine, MS m/e 314 (M+).

nmr (CDCl₃) δ1.6 (d, 3H), 1.9 (2s, 6H), 4.2–4.7 (m, 4H), 5.5 (t, 1H), 6.8–6.9 (m, 6H), 7.3–7.7 (m, 1H) and 8.0–8.2 ppm (m, 1H).

In the same way, 2-{2-methyl-2-[4-(3-methyl-2-butenoxy)phenoxy]ethoxy}pyridine is prepared from 2-chloropyridine and the sodium salt of 2-methyl-2-[4-(3-methyl-2-butenoxy)phenoxy]ethanol.

EXAMPLE 3

To a mixture of sodium hydride (0.12 g) in 5 ml of THF and 4 ml of HMPA, cooled in an ice bath, is added, dropwise, a solution of 2-[4-(1-methylpropoxy)phenoxy]ethanol (1.00 g) in 5 ml of THF. The mixture is stirred at RT for 2 hours, after which 2,6-difluoropyridine (0.65 g) is added and the mixture is stirred at RT overnight. The THF is removed by rotoevaporation and the product is isolated by column chromatography on silica gel to give 6-fluoro-2-{2-[4-(1-methylpropoxy)phenoxy]ethoxy}pyridine, MS m/e 306 (M+).

nmr (CDCl₃) δ0.8–1.9 (m, 8H), 3.9–4.4 (m, 3H), 4.5–4.7 (m, 2H), 6.3–6.7 (m, 2H), 6.8 (s, 4H) and 7.3–7.8 ppm (q, 1H).

Following the same procedures, the sodium salt of 2-[4-(1-methylpropoxy)phenoxy]ethanol is reacted with 2,6-dichloropyridine to give 6-chloro-2-{2-[4-(1-methylpropoxy)phenoxy]ethoxy}pyridine.

In the same way, 2,6-difluoropyridine is reacted with the sodium salt of each of 1-methyl-2-[4-(1-methylpropoxy)phenoxy]ethanol, 2-methyl-2-[4-(1-methylpropoxy)phenoxy]ethanol and 2-[4-(3-methyl-2-butenoxy)phenoxy]ethanol to give, respectively, 6-fluoro-2-{1-methyl-2-[4-(1-methylpropoxy)phenoxy]ethoxy}pyridine, 6-fluoro-2-{2-methyl-2-[4-(1-methylpropoxy)phenoxy]ethoxy}pyridine, and 6-fluoro-2-{2-[4-(3-methyl-2-butenoxy)phenoxy ]ethoxy}pyridine.

EXAMPLE 4

To sodium hydride (0.17 g, 7.14 mmol) in 10 ml of dimethylformamide (DMF) is added, at RT, 2-[4-(1-methylpropoxy)phenoxy]ethanol (1.50 g, 7.14 mmol) in 3 ml of DMF. The mixture is heated to 50° and stirred for 1 hour. 2-Chloropyrimidine (0.94 g, 8.21 mmol) is then added, at 55°, and the mixture is stirred for 1 hour and then cooled to RT. The reaction mixture is poured into ice water and extracted with ether. The combined organic layers are washed with water until neutral and with brine, dried and filtered and the solvent is removed to give, following purification of the residue by preparative thin layer chromatography (prep. TLC), 2-{2-[4-(1-methylpropoxy)phenoxy]ethoxy}pyrimidine, MS m/e 289 (M+ +H).

nmr (CDCl₃) δ0.95 (m, 3H), 1.23 (d, 3H, J=6 Hz), centered at 4.18 and 4.23 (m, 5H) and 8.53 ppm (d, 2H, J=5 Hz).

In the same manner, the sodium salt of 1-methyl-2-[4-(1-methylpropoxy)phenoxy]ethanol and 2-chloropyrimidine are reacted together to give 2-{1-methyl-2-[4-(1-methylpropoxy)phenoxy]ethoxy}pyrimidine, MS m/e 320 (M+ +NH₄).

nmr (CDCl₃) δ0.96 (m, 3H), 1.25 (d, 3H, J=6 Hz), 1.50 (d, 3H, J=6 Hz), 5.57 (sextet, 1H, J=6 Hz) and 8.54 ppm (d, 2H, J=5 Hz).

Following the same procedures, the sodium salt of each of 2-methyl-2-[4-(1-methylpropoxy)phenoxy]ethanol, 2-[4-(1-methylpropylthio)phenoxy]ethanol, 1-methyl-2-[4-(1-methylpropylthio)phenoxy]ethanol, 2-[4-(3-methyl-2-butenoxy)phenoxy]ethanol, 2-(4-isopropoxyphenoxy)ethanol and 2-[4-(1-ethylpropoxy)phenoxy]ethanol is reacted with 2-chloropyrimidine to give, respectively, 2-{2-methyl-2-[4- (1-methylpropoxy)phenoxy]ethoxy}pyrimidine, 2-{2-[4-(1-methylpropylthio)phenoxy]ethoxy}pyrimidine, [nmr (CDCl₃) δ0.8–1.1 (t, 3H), 1.2 (d, 3H), 1.2–1.7 (m, 2H), 1.7–2.2 (h, 1H), 4.2–4.9 (m, 4H), 6.9 (d, 2H), 6.8–7.1 (m, 1H), 7.4 (d, 2H) and 8.5 ppm (d, 2H)], 2-{1-methyl-2-[4-(1-methylpropylthio)phenoxy]ethoxy}pyrimidine, [nmr (CDCl₃) δ0.8–1.1 (t, 3H), 1.2 (d, 3H), 1.3–1.9 (m, 2H) , 2.7–3.3 (h, 1H), 3.9–4.6 (m, 2H), 5.4–5.7 (h, 1H), 6.8 (d, 2H), 6.7–7.1 (m, 1H), 7.3 (d, 2H) and 8.5 ppm (d, 2H)], 2-{2-[4-(3-methyl-2-butenoxy)phenoxy]ethoxy}pyrimidine, [nmr (CDCl₃) δ1.6–1.8 (2ds, 6H), 4.2–4.8 (m, 6H), 5.3–5.6 (t, 1H), 6.9 (s, 4H), 6.8–7.0 (m, 1H) and 8.5 ppm (d, 2H)], 2-[2-(4-isopropoxyphenoxy)ethoxy]pyrimidine, [nmr (CDCl₃) δ1.2 (d, 6H), 4.2–4.8 (m, 5H), 6.8 (s, 4H), 6.8–7.0 (m, 1H) and 8.4 ppm (d, 2H)], and 2-{2-[4-(1-ethylpropoxy)phenoxy]ethoxy}pyrimidine, [nmr (CDCl₃) δ0.9 (t, 6H), 1.2–1.9 (m, 4H), 4.0 (p, 1H), 4.2–4.4 (m, 2H), 4.6–4.9 (m, 2H), 6.9 (s, 4H), 6.8–7.0 (m, 1H) and 8.5 (d, 2H)].

EXAMPLE 5

To sodium hydride (0.35 g, 14.6 mmol) in 20 ml of DMF at RT is slowly added 2-mercaptopyrimidine (1.64 g, 14.6 mmol) in 30 ml of DMF, keeping the temperature of the reaction at 30° or below. After anion formation is complete, 2-[4-(1-methylpropoxy)phenoxyethyl bromide (4.0 g, 14.6 mmol) is slowly added, with cooling to keep the reaction temperature at 15°–20°. The mixture is then stirred at RT for 18 hours, after which it is poured into water and extracted with ether. The combined organic layers are washed with water and with brine, dried and filtered and the solvent is removed to give, after purification by prep. TLC, 2-{2-[4-(1-methylpropoxy)phenoxy]ethylthio}pyrimidine, MS m/e 305 (M+ +H).

nmr (CDCl$_3$) δ0.95 (m, 3H), 1.23 (d, 3H, J=6 Hz), 3.52 (m, 2H), and 8.53 ppm (d, 2H, J=5 Hz).

Following the same procedures, the sodium salt of 2-mercaptopyrimidine is reacted with each of 2-[4-(1-methylpropylthio)phenoxy]ethyl bromide, 1-methyl-2-[4-(1-methylpropoxy)phenoxy]phenoxy]ethyl bromide, 2-[4-(3-methyl-2-butenoxy)phenoxy]ethyl bromide, 2-[4-(1-methyl-n-butoxy)phenoxy]ethyl bromide, 2-[4-(1-methylpentoxy)phenoxy]ethyl bromide and 2-[4-(1,3-dimethyl-n-butoxy)phenoxy]ethyl bromide to give, respectively, 2-{2-[4-(1-methylpropylthio)phenoxy]ethylthio}pyrimidine, [nmr (CDCl$_3$) δ0.18–1.1 (t, 3H), 1.2 (d, 3H), 1.2–1.8 (m, 2H), 2.7–3.3 (h, 6H), 3.4–3.7 (t, 2H), 4.2–4.4 (t, 2H), 6.8–7.0 (m, 1H), 7.4 (d, 2H) and 8.5 ppm (d, 2H)];

2-{1-methyl-2-[4-(1-methylpropoxy)phenoxy]ethylthio}pyrimidine;

2-{2-[4-(3-methyl-2-butenoxy)phenoxy]ethylthio}pyrimidine;

2-{2-[4-(1-methyl-n-butoxy)phenoxy]ethylthio}pyrimidine, [nmr (CDCl$_3$) δ0.94 (m, 3H), 1.24 (d, 3H, J=6 Hz), 3.50 (t, 2H, J=7 Hz), 4.22 (t, 2H, J=7 Hz), 6.85 (s, 4H) and 8.49 ppm (d, 2H, J=5 Hz)];

2-{2-[4-(1-methylpentoxy)phenoxy]ethylthio}pyrimidine, [nmr (CDCl$_3$) δ0.90 (m, 3H), 1.25 (d, 3H, J=6 Hz), 3.51 (m, 2H), centered at 4.19 (m, 3H), 6.84 (m, 4H) and 8.51 ppm (d, 2H, J=5 Hz)]; and 2-{2-[4-(1,3-dimethyl-n-butoxy)phenoxy]ethylthio}pyrimidine, [nmr (CDCl$_3$) δ0.92 (m, 6H), 1.23 (d, 3H, J=6 Hz), 3.50 (t, 2H, J=7 Hz), 4.21 (m, 2H), 6.84 (s, 4H) and 8.49 ppm (d, 2H, J-5 Hz)].

EXAMPLE 6

To sodium hydride; (0.55 g) in 5 ml of DMF is added 2-[4-(1-methylpropoxy)phenoxy]ethanol (2.0 g) in 10 ml of DMF, and the mixture is stirred at RT for 1.25 hours. 2-Chloro-1,3-thiazole (1.36 g) in 5 ml of DMF is then added, and the mixture is stirred at RT overnight. The reaction mixture is poured into water and extracted with ether. The combined organic layers are washed with water and with brine, dried and filtered and the solvent is removed by rotoevaporation. The resulting oil is purified by column chromatography to give 2-{2-[4-(1-methylpropoxy)phenoxy]ethoxy}-1,3-thiazole.

nmr (CDCl$_3$) δ0.95 (t, 3H, J=7.25 Hz), 1.24 (d, 3H, J=5.9 Hz), 1.62 (m, 2H), 4.12 (m, 3H), 4.72 (m, 2H), 6.65 (d, 1H, J=2.2 Hz) and 7.09 ppm (d, 1H, J=3.7 Hz).

Following the above procedures, 2-chloro-1,3-thiazole is reacted with the sodium salt of each of 1-methyl-2-[4-(1-methylpropoxy)phenoxy]ethanol, 2-methyl-2-[4-(1-methylpropoxy)phenoxy]ethanol, 2-[4-(1-methylpropylthio)phenoxy]ethanol and 2-[4-(3-methyl-2-butenoxy)phenoxy]ethanol to give, respectively, 2-{1-methyl-2-[4-(1-methylpropoxy)phenoxy]ethoxy}-1,3-thiazole, [nmr (CDCl$_3$) δ0.95 (t, 3H), 1.23 (d, 3H, J=5.9 Hz), 1.60 (m, 5H), 4.11 (m, 3H), 5.44 (m, 1H), 6.62 (d, 1H, J=3.7 Hz) 6.82 (s, 4H) and 7.09 ppm (d, 1H, J=3.9 Hz)];

2-{2-methyl-2-[4-(1-methylpropoxy)phenoxy]ethoxy}-1,3-thiazole;

2-{2-[4-(1-methylpropylthio)phenoxy]ethoxy}-1,3-thiazole, [nmr (CDCl$_3$) δ0.98 (m, 3H), 1.21 (d, 3H, J=7 Hz), centered at 4.29 and 4.75 (m, 4H), 6.67 (d, 1H, J=4 Hz), 6.86 (m, 2H), 7.11 (d, 1H, J=4 Hz) and 7.37 ppm (m, 2H)]; and 2-{2-[4-(3-methyl-2-butenoxy)phenoxy]ethoxy}-1,3-thiazole, [nmr (CDCl$_3$) δ1.72 (d, 6H, J=5.5 Hz), 4.20 (m, 2H), 4.41 (d, 2H, J=6.6 Hz), 4.69 (m, 2H), 6.62 (m, 1H), 6.82 (s, 4H) and 7.08 ppm (m, 1H)].

In the same way, 2-chloro-2-thiazoline is reacted with the sodium salt of each of 2-[4-(1-methylpropoxy)-phenoxy]ethanol and 1-methyl-2-[4-(1-methylpropoxy)-phenoxy]ethanol to give, respectively, 2-{2-[4-(1-methylpropoxy)phenoxy]ethoxy}-2-thiazoline, and 2-{1-methyl-2-[4-(1-methylpropoxy)phenoxy]ethoxy}-2-thiazoline.

EXAMPLE 7

To sodium hydride (0.42 g) in 5 ml of DMF is added 2-mercapto-2-thiazoline (1.05 g) in 5 ml of DMF, and the mixture is stirred at RT for 1 hour. 2-[4-(1-Methylpropoxyphenoxy]ethyl bromide (2.00 g) in 5 ml of DMF is added dropwise and the mixture is stirred at RT for 72 hours, after which it is worked up as in Example 6 to give 2-{2-[4-(1-methylpropoxy)phenoxy]ethylthio}-2-thiazoline.

nmr (CDCl$_3$) δ0.96 (t, 3H, J=7.5 Hz), 1.25 (d, 3H, J=6.2 Hz), 1.66 (m, 2H), 3.44 (m, 4H), 4.21 (m, 5H) and 6.82 ppm (s, 4H).

Following the above procedures, the sodium salt of 2-mercapto-2-thiazoline is reacted with each of 2-[4-(1-methylpropylthio)phenoxy]ethyl bromide, 1-methyl-2-[4-(1-methylpropoxy)phenoxy]ethyl bromide and 2-[4-(3-methyl-2-butenoxy)phenoxy]ethyl bromide to give, respectively, 2-{2-[4-(1-methylpropylthio)phenoxy]ethylthio}-2-thiazoline, [nmr (CDCl$_3$) δ0.98 (m, 3H), 1.20 (d, 3H, J=7 Hz), 3.42 (m, 4H), 4.21 (m, 4H), 6.85 (m, 2H) and 7.36 ppm (m, 2H)];

2-{1-methyl-2-[4-(1-methylpropoxy)phenoxy]ethylthio}-2-thiazoline; and

2-{2-[4-(3-methyl-2-butenoxy)phenoxy]ethylthio}-2-thiazoline.

In the same way, the sodium salt of 2-mercapto-1,3-thiazole is prepared and reacted with each of 2-[4-(1-methylpropoxy)phenoxy]ethyl bromide and 1-methyl-2-[4-(1-methylpropoxy)phenoxy]ethyl bromide to give, respectively, 2-{2-[4-(1-methylpropoxy)phenoxy]ethylthio}-1,3-thiazole, and 2-{1-methyl-2-[4-(1-methylpropoxy)phenoxy]ethylthio}-1,3-thiazole.

EXAMPLE 8

Following the procedures of Examples 5 and 7, the sodium salt of 2-mercaptopyridine is prepared and is then reacted with each of 2-[4-(1-methylpropoxy)-phenoxy]ethyl bromide, 2-[4-(1-methylpropylthio)-phenoxy]ethyl bromide, 1-methyl-2-[4-methylpropoxy)phenoxy]ethyl bromide and 2-[4-(3-methyl-2-butenoxy)phenoxy]ethyl bromide to give, respectively, 2-{2-[4-(1-methylpropoxy)phenoxy]ethylthio}pyridine, [nmr (CDCl₃) δ0.8–1.1 (t, 3H), 1.1–1.3 (d, 3H), 1.3–1.9 (m, 2H), 3.4–3.7 (t, 2H), 4.0–4.3 (m, 3H), 6.9 (s, 4H), 6.7–7.6 (m, 3H) and 8.4 ppm (d, 1H)];

2-{2-[4-(1-methylpropylthio)phenoxy]ethylthio}pyridine,

2-{1-methyl-2-[4-(1-methylpropoxy)phenoxy]ethylthio}pyridine, and

2-{2-[4-(3-methyl-2-butenoxy)phenoxy]ethylthio}pyridine.

EXAMPLE 9

N-chlorosuccinimide (1.05 g, 7.9 mmol) is added in portions to 2-{2-[4-(1-methylpropoxy)phenoxy]ethylthio}pyrimidine (2.0 g, 6.6 mmol) in carbon tetrachloride at 5°. The mixture is warmed to RT and stirred for 18 hours, followed by heating to 60° for 32 hours. The reaction mixture is filtered and the solvent is removed to give, following purification by chromatography, 2-{1-chloro-2-[4-(1-methylpropoxy)phenoxy]ethylthio}pyrimidine, MS m/e 338 (M+).

nmr (CDCl₃) δ0.97 (m, 3H), 1.25 (d, 3H, J=6 Hz), 4.22 (m, 1H, J=6 Hz), 4.46 (d, 2H, J=6 Hz), 6.38 (t, 1H, J=6Hz) and 8.64 ppm (d, 2H, J=5 Hz).

EXAMPLE 10

The compounds (a) 2-{2-[4-(1-methylpropoxy)phenoxy]ethoxy}pyridine, (b) 2-{1-methyl-2-[4-(1-methylpropoxy)phenoxy]ethoxy}pyridine, (c) 6-fluoro-2-}2-[4-(1-methylpropoxy)phenoxy]ethoxy}pyridine, and (d) 2-{2-[4-(1-methylpropoxy)phenoxy]ethoxy}pyrimidine were tested for contact activity on houseflies by the following method.

Third instar, post-feeding wandering *Musca domestica* L. larvae are individually treated topically with 1 μl of the test compound in acetone at different dose rates. Additional larvae are treated identically with 1 μl of acetone as the control. Larvae are held in covered containers for 7 days at 31° and 16 hour photoperiod. The assay effect is expressed as $ED_{50}$, which is the dose, in g per larva, required to cause an effect in 50% of the test insects. Effects observed include direct toxicity (larval death); delayed toxicity (pupal death); and juvenile hormone activity, such as failure of adults to emerge completely, chitin inhibition, distortion of cuticle and pupation abnormalities. Each of the above tested compounds had an $ED_{50}$ of less than 0.0050 μg/larva.

EXAMPLE 11

The compounds (a) 2-{2-[4-(1-methylpropoxy)phenoxy]ethoxy}pyridine, and (b) 2-{1-methyl-2-[4-(1-methylpropoxy)phenoxy]ethoxy}pyridine were tested for activity on the yellow fever mosquito as follows.

Late fourth instar *Aedes aegypti* larvae (generally 5 days post-hatching) are placed in plastic containers with 50 ml tap water into which has been mixed 50 μl of acetone dilution of the test compound at the concentration to be tested. A few drops of a liver powder suspension are added as a food source. The containers are covered and held at 28°, 16 hour photoperiod until all larvae or pupae are either dead or have emerged as adults. The assay effect is expressed as $EC_{50}$, which is the concentration, in ppm required to cause an effect in 50% of the test insects. Effects observed include direct toxicity (larval death) and juvenile hormone activity such as pupal mortality and failure of adults to emerge completely. Each of the above tested compounds had an $EC_{50}$ of less than 0.0050 ppm.

EXAMPLE 12

Following the procedure of Example 1, 2-[4-(1-methyl-n-butoxy)phenoxy]ethanol (0.80 g, 3.6 mmol) in 5 ml of DMF is added to sodium hydride (0.26 g, 5.3 mmol) in 5 ml of DMF, followed by addition of 2-chloropyridine (0.50 g, 5.3 mmol) to give 2-{2-[4-(1-methyl-n-butoxy)phenoxy]ethoxy}pyridine.

nmr (CDCl₁₃) δ0.94 (m, 3H), 1.24 (d, 3H, J=6 Hz), 4.25 (m, 2H), 4.65 (m, 2H), 6.85 (s, 4H), 7.54 (m, 1H) and 8.13 ppm (m, 1H).

In the same way, 2-chloropyridine is reacted with the sodium salt of each of 2-[4-(1-methylpentoxy)phenoxy]ethanol, 2-[4-(1-ethylpropoxy)phenoxy]ethanol and 2-(4-isopropoxyphenoxy)ethanol to give, respectively, 2-{2-[4-(1-methylpentoxy)phenoxy]ethoxy}pyridine, [nmr (CDCl₃) δ0.90 (m, 3H), 1.24 (d, 3H, J=6 Hz), 4.25 (m, 2H), 4.65 (m, 2H), 6.84 (s, 4H), 7.54 (m, 1H) and 8.13 ppm (m, 1H)];

2-{2-[4-(1-ethylpropoxy)phenoxy]ethoxy}pyridine, [nmr (CDCl₃) δ8 0.95 (t, 6H), 1.2–2.0 (m, 4H), 3.8–4.2 (p, 1H), 4.2–4.4 (t, 2H), 4.5–4.8 (t, 2H), 6.7–7.0 (m, 2H), 6.8 (s, 4H), 7.3–7.7 (m, 1H) and 8.0–8.3 ppm (m, 1H)]; and 2-[2-(4-isopropoxyphenoxy)ethoxy]pyridine, [nmr (CDCl₃) δ1.2 (d, 6H), 4.1–4.8 (m, 5H), 6.8 (s, 4H), 6.7–7.8 (m, 3H) and 8.0–8.5 ppm (m, 1H)].

EXAMPLE 13

Following the procedure of Example 6, 1-methyl-2-[4-(1-methylpropylthio)phenoxy]ethanol (1.60 g, 6.7 mmol) is treated with sodium hydride (0.48 g, 10.0 mmol), and the resulting sodium salt is reacted with 2-bromo-1,3-thiazole (800 1, 8.7 mmol) to give 2-{1-methyl-2-[4-(1-methylpropylthio)phenoxy]ethoxy}-1,3-thiazole.

nmr (CDCl₃) δ0.98 (m, 3H), 1.2 (d, 3H, J=7 Hz), 1.52 (d, 3H, J=7 Hz), 2.95 (m, 1H), 4.14 (m, 2H), 5.43 (m, 1H), 6.64 (d, 1H, J=4 Hz), 6.84 (m, 2H), 7.11 (d, 1H, J=4 Hz) and 7.36 ppm (m, 2H).

In the same manner, 2-bromo-1,3-thiazole is reacted with the sodium salt of each of 2-[4-(1-methyl-n-butoxy)phenoxy]ethanol, 2-[4-(1-methylpentoxy)phenoxy]ethanol, 2-[4-(1,3-dimethyl-n-butoxy)phenoxy]ethanol, 2-(4-isopropoxyphenoxy)ethanol, 2-[4-(1-ethylpropoxy)phenoxy]ethanol and 2-[4-(1-methylpropoxy)phenoxy]ethylthiol to give, respectively, 2-{2-[4-(1-methyl-n-butoxy)phenoxy]ethoxy}-1,3-thiazole, [nmr (CDCl₃) δ0.94 (m, 3H), 1.25 (d, 3H, J=6 Hz), centered at 4.26 (m, 2H), centered at 4.74 (m, 2H), 6.68 (m, 1H), 6.83 (s, 4H) and 7.11 ppm (m, 1H)];

2-{2-[4-(1-methylpentoxy)phenoxy]ethoxy}-1,3-thiazole, [nmr (CDCl₃) δ0.90 (m, 3H), 1.25 (d, 3H, J=6 Hz), 4.05–4.31 (m, 3H), 4.73 (m, 2H), 6.67 (d, 1H, J=4 Hz), 6.83 (s, 4H) and 7.11 ppm (d, 1H, J=4 Hz)];

2-{2-[4-(1,3-dimethyl-n-butoxy)phenoxy]ethoxy}-1,3-thiazole, [nmr (CDCl₃) δ0.92 (m, 6H), 1.21 (d, 3H, J=6 Hz), centered at 4.25 (m, 2H), centered at 4.73 (m, 2H), 6.68 (m, 1H), 6.75 (s, 4H) and 7.12 (m, 1H)];

2-[2-(4-isopropoxyphenoxy)ethoxy]-1,3-thiazole, [nmr (CDCl₃) δ1.2 (d, 6H), 4.1–4.8 (m, 5H), 6.6 (d, 1H), 6.8 (s, 4H) and 7.1 ppm (d, 1H)];

2-{2-[4-(1-ethylpropoxy)phenoxy]ethoxy}-1,3-thiazole, [nmr (CDCl₃) δ0.95 (t, 6H), 1.20–1.9 (m, 4H), 3.8–4.2 (m, 1H), 4.1–4.4 (m, 2H), 4.6–4.8 (m, 2H), 6.6 (d, 1H), 6.8 (s, 4H) and 7.1 (d, 1H)]; and 2-{-2-[4-(1-methylpropoxy)phenoxy]ethylthio}-1,3thiazole, [nmr (CDCl₃) δ0.96 (m, 3H), 1.24 (d, 3H, J=6 Hz), 3.57 (m, 2H), 4.07–4.30 (m, 3H), 6.80 (s, 4H), 7.19 (m, 1H) and 7.65 (m, 1H)].

EXAMPLE 14

Generally following the procedure of Example 7, 2-mercapto-2-thiazoline (0.67 g, 5.6 mmol) is treated with sodium hydride (0.35 g, 7.3 mmol), with cooling, and the resulting sodium salt is reacted with 1-methyl-2-[4-(1methylpropylthio)phenoxy]ethyl bromide (1.70 g, 5.6 mmol) at RT to give 2-{1-methyl-2-[4-(1-methylpropylthio)phenoxy]ethylthio}-2-thiazoline.

nmr (CDCl₃) δ0.97 (m, 3H), 1.19 (d, 3H, J=7 Hz), 1.46 (d, 3H, J=7 Hz), 2.94 (m, 1H), 3.32 (t, 3H, J=8 Hz), 3.92–4.29 (m, 4H), 6.88 (m, 2H) and 7.35 ppm (m, 2H).

In the same manner, 2-mercapto-2-thiazoline is reacted with each of 2-[4-(1-methyl-n-butoxy)phenoxy]ethyl bromide, 2-[4-(1-methylpentoxy)phenoxy]ethyl bromide, 2-[4-(1,3-dimethyl-n-butoxy)phenoxy]ethyl bromide and 2-[4-(1-ethylpropoxy)phenoxy]ethyl bromide to give, respectively, 2-{2-[4-(1-methyl-n-butoxy)phenoxy]ethylthio}-2-thiazoline, [nmr (CDCl₃) δ0.94 (m, 3H), 1.25 (d, 3H, J=6 Hz), 3.30–3.51 (m, 4H), 4.11–4.30 (m, 4H) and 6.82 ppm (s, 4H)];

2-{2-[4-(1-methylpentoxy)phenoxy]ethylthio}-2-thiazoline, [nmr (CDCl₃) δ0.90 (m, 3H), 1.24 (d, 3H, J=6 Hz), centered at 3.39 (m, 4H), centered at 4.19 (m, 5H) and 6.81 ppm (s, 4H)];

2-{2-[4-(1,3-dimethyl-n-butoxy)phenoxy]ethylthio}-2-thiazoline, [nmr (CDCl₃) δ0.92 (m, 6H), 1.23 (d, 3H, J=6 Hz), centered at 3.40 (m, 4H), 3.99–4.40 (m, 5H) and 6.82 ppm (s, 4H)]; and 2-{2-[4-(1-ethylpropoxy)phenoxy]ethylthio}-2-thiazoline, [nmr (CDCl₃) δ0.95 (tt, 6H), 1.2–1.9 (m, 4H), 3.4 (q, 4H), 3.8–4.3 (m, 5H) and 6.9 ppm (s, 4H)].

EXAMPLE 15

A mixture of 2-(4-isopropoxyphenoxy)ethanol (3.50 g), mesyl chloride (2.20 g) and triethylamine (2.0 g) in 20 ml of methylene chloride is stirred at RT for 3 hours. It is then poured into water and extracted with methylene chloride. The solvent is removed from the combined organic layers by rotoevaporation, and the residue is purified by column chromatography to give 2-(4-isopropoxyphenoxy)ethyl methanesulfonate.

Following the procedure of Example 7, 2-mercapto-2-thiazoline (0.77 g) is treated with sodium hydride (0.32 g), and the resulting sodium salt is reacted with the above methanesulfonate (1.50 g) to give 2-[2-(4-isopropoxyphenoxy)ethylthio]-2-thiazoline.

nmr (CDCl₃) δ1.2 (d, 6H), 3.2–3.6 (m, 4H), 4.1–4.6 (m, 5H) and 6.8 ppm (s, 4H).

What is claimed is:

1. A compound of the formula

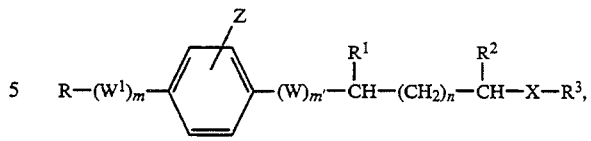

wherein
R is $C_{4-8}$alkyl, $C_{4-8}$alkenyl, $C_{4-8}$alkadienyl, $C_{4-8}$alkynyl or $C_{4-8}$alkadiynyl,
$R^1$ is hydrogen or $C_{1-5}$alkyl,
$R^2$ is hydrogen, $C_{1-5}$alkyl or halo,
with the proviso that at least one of $R^1$ and $R^2$ is hydrogen,

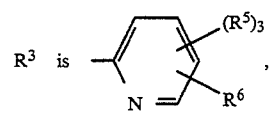

wherein
each $R^5$ and $R^6$, is independently hydrogen, halo, $C_{1-8}$alkyl, $C_{1-8}$alkoxy, $C_{1-8}$alkylthio, nitro, methyl substituted by 1 to 3 halos, ethyl substituted by 1 to 5 halos or $C_{3-8}$alkyl substituted by 1 to 6 halos,
W is oxygen or sulfur,
$W^1$ is oxygen or sulfur,
X is oxygen or sulfur,
Z is hydrogen, $C_{1-5}$alkyl, halo, methyl substituted by 1 to 3 halos, ethyl substituted by 1 to 5 halos or $C_{3-5}$alkyl substituted by 1 to 6 halos,
m is 0 or 1,
m' is 0 or 1, and
n is 0.

2. A compound according to claim 1 wherein
$R^1$ is hydrogen or methyl,
$R^2$ is hydrogen or methyl, with the proviso that at least one of $R^1$ and $R^2$ is hydrogen,
each $R^5$ and $R^6$ is independently hydrogen or halo, and
W is oxygen.

3. A compound according to claim 2 wherein
R is $C_{4-8}$alkyl, $C_{4-8}$alkenyl or $C_{4-8}$alkadienyl, and each $R^5$, is hydrogen.

4. A compound according to claim 3 wherein
R is 1-methylpropyl, 1-methylbutyl, 1,3-dimethylbutyl or 3-methyl-2-butenyl, and
$R^1$ is hydrogen.

5. A compound according to claim 4 wherein R is 1-methylpropyl, 1-methylbutyl or 1,3-dimethylbutyl.

6. A compound according to claim 1 wherein $R^3$ is

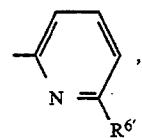

wherein $R^{6'}$ is hydrogen or halo.

7. A compound according to claim 6 where in $R^{6'}$ is hydrogen.

8. A compound according to claim 1 wherein
$R^1$ is hydrogen or methyl,
$R^2$ is hydrogen or methyl, with the proviso that at least one of $R^1$ and $R^2$ is hydrogen, each $R^5$ and $R^6$ is independently hydrogen or halo, and W is oxygen.

9. A compound according to claim 8 wherein
R is $C_{4-8}$alkyl, $C_{4-8}$alkenyl or $C_{4-8}$alkadienyl, and
each $R^5$ is hydrogen.

10. A compound according to claim 9 wherein
R is $C_{4-8}$alkyl or 3-methyl-2-butenyl,
$R^3$ is

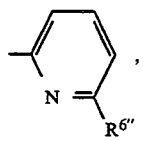

wherein
$R^{6''}$ is hydrogen, fluoro or chloro,
Z is hydrogen,
m is 1, and
m' is 1.

11. A compound according to claim 10 wherein R is 1-methylpropyl, 1-methylbutyl, 1-methylpentyl, 1-ethylpropyl or 3-methyl-2-butenyl.

12. A compound according to claim 11 wherein R is 1-methylpropyl or 3-methyl-2-butenyl.

13. A compound according to claim 12 wherein $R^{6''}$ is hydrogen.

14. A compound according to claim 9 wherein
R is 1-methylpropyl, 1-methylbutyl, 1,3-dimethylbutyl or 3-methyl-2-butenyl, and
$R^1$ is hydrogen.

15. A compound according to claim 14 wherein R is 1-methylpropyl, 1-methylbutyl or 1,3-dimethylbutyl.

16. A compound according to claim 14 wherein $R^3$ is

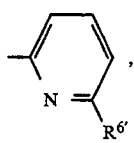

wherein
$R^{6'}$ is hydrogen or halo.

17. A compound according to claim 16 wherein $R^{6'}$ is hydrogen.

18. A compound according to claim 16 wherein
R is 1-methylpropyl, 1-methylbutyl or 3-methyl-2-butenyl,
X is oxygen, and
$W^1$ is oxygen.

19. A compound according to claim 18 where in $R^{6'}$ is hydrogen.

20. The compound according to claim 19 which is 2-{2-[4-(1-methylpropoxy)phenoxy]ethoxy}pyridine.

21. The compound according to claim 19 which is 2-{1-methyl-2-[4-(1-methylpropoxy)phenoxy]ethoxy}pyridine.

22. The compound according to claim 19 which is 2-{2-[4-(3-methyl-2-butenoxy)phenoxy]ethoxy}pyridine.

23. The compound according to claim 19 which is 2-{2-[4-(1-methylbutoxy)phenoxy]ethoxy}pyridine.

24. The compound according to claim 9 which is 2-{2-methyl-2-[4-(1-methylpropoxy)phenoxy]ethoxy}pyridine.

25. A pesticidal composition comprising a pesticidally effective amount of compound according to claim 1 and a carrier.

26. A method of combatting pests comprising applying to a pest or its locus a pest-controlling amount of a compound according to claim 1.

* * * * *